(12) United States Patent
Guinan

(10) Patent No.: US 10,747,848 B2
(45) Date of Patent: Aug. 18, 2020

(54) SYSTEM AND METHOD FOR MEDICAL BILLING SYSTEMS TO SUBMIT TRANSACTIONS FOR SERVICES COVERED UNDER PHARMACY BENEFITS

(71) Applicant: POC NETWORK TECHNOLOGIES, INC., Coral Gables, FL (US)

(72) Inventor: John Paul Guinan, Miami, FL (US)

(73) Assignee: POC NETWORK TECHNOLOGIES, INC., Coral Gables, FL (US)

(*) Notice: Subject to any disclaimer, the term of this patent is extended or adjusted under 35 U.S.C. 154(b) by 627 days.

(21) Appl. No.: 14/445,827

(22) Filed: Jul. 29, 2014

(65) Prior Publication Data

US 2015/0149197 A1 May 28, 2015

Related U.S. Application Data

(60) Provisional application No. 61/907,584, filed on Nov. 22, 2013.

(51) Int. Cl.
| | |
|---|---|
| *G06Q 10/00* | (2012.01) |
| *G06Q 50/00* | (2012.01) |
| *G06F 19/00* | (2018.01) |
| *G06Q 20/02* | (2012.01) |
| *G06Q 50/22* | (2018.01) |
| *G06Q 30/04* | (2012.01) |

(52) U.S. Cl.
CPC ......... *G06F 19/328* (2013.01); *G06Q 20/023* (2013.01); *G06Q 20/027* (2013.01); *G06Q 30/04* (2013.01); *G06Q 50/22* (2013.01)

(58) Field of Classification Search
CPC ............................. G06F 19/328; G06Q 20/14
USPC ......................................................... 705/2, 3
See application file for complete search history.

(56) References Cited

U.S. PATENT DOCUMENTS

| 8,321,243 B1* | 11/2012 | Harris, Sr. | G06Q 10/10 705/3 |
|---|---|---|---|
| 8,447,627 B1* | 5/2013 | Cruise | G06F 19/328 705/2 |
| 2004/0006490 A1* | 1/2004 | Gingrich | G06F 19/328 705/2 |
| 2004/0064386 A1* | 4/2004 | Goguen | G06Q 30/04 705/34 |
| 2005/0102170 A1* | 5/2005 | Lefever | G06Q 30/02 705/4 |
| 2005/0288972 A1* | 12/2005 | Marvin | G06F 19/328 705/4 |

(Continued)

*Primary Examiner* — Trang T Nguyen
(74) *Attorney, Agent, or Firm* — Stetina Brunda Garred and Brucker

(57) ABSTRACT

A system and method for medical offices and other non-pharmacy providers using management systems or other billing systems based on the ASC X12 transaction standards to perform eligibility transactions, perform benefit predetermination transactions and to submit claims to pharmacy insurance companies or their pharmacy benefit managers that must receive the transactions as real-time transactions based on the NCPDP transaction standards are disclosed. Same medical offices and non-pharmacy providers can receive electronic remittance advice files from pharmacy insurance companies or their pharmacy benefit managers that contain data formatted and using identifiers that relate to the initial ASC X12 claims submitted.

14 Claims, 5 Drawing Sheets

(56) References Cited

U.S. PATENT DOCUMENTS

| | | | |
|---|---|---|---|
| 2007/0027718 A1* | 2/2007 | Amerantes | G06Q 50/24 |
| | | | 705/3 |
| 2007/0143665 A1* | 6/2007 | Machiraju | G06F 17/2247 |
| | | | 715/236 |
| 2008/0288281 A1* | 11/2008 | Shell | G06Q 10/10 |
| | | | 705/2 |
| 2009/0030727 A1* | 1/2009 | Revak | G06Q 10/00 |
| | | | 705/3 |
| 2009/0326974 A1* | 12/2009 | Tolan | G06Q 10/04 |
| | | | 705/2 |
| 2012/0029950 A1* | 2/2012 | Lyle | G06F 19/328 |
| | | | 705/4 |

* cited by examiner

SYSTEM AND METHOD FOR MEDICAL BILLING SYSTEMS TO SUBMIT TRANSACTIONS FOR SERVICES COVERED UNDER PHARMACY BENEFITS

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates to medical information management, and more particularly to a system and method for billing insurance companies or their pharmacy benefit managers for services performed by medical providers and other non-pharmacy providers for services covered under pharmacy benefits.

2. Related Art

The business processes and management systems for physician offices, medical insurance companies and other entities involved in providing services covered under medical benefits have developed and evolved separately from the business processes and systems for the pharmacy providers, pharmacy insurance companies and pharmacy benefit managers involved with processing claims for services covered under pharmacy benefits. Two completely different sets of business and transaction standards have been formed and have been entrenched in each of the two parts of the healthcare service market. As a result, two completely separate national data transaction processing infrastructures each with their own participants have been created in the country: one for pharmacy services, and the other for medical services. Recently, physician offices and other medical providers such as retail pharmacy clinics have begun to perform services for patients that are covered by the patient's pharmacy insurance coverage such as administering preventative vaccines or dispensing drug products. The dichotomy of claims processing infrastructures make it very difficult or impossible for medical providers to submit claims using their current medical billing systems to pharmacy insurance companies or their pharmacy benefit managers for services covered by pharmacy insurance benefits. This problem has severely inhibited the growth of the practice of medical providers to perform services such as vaccinations, which in addition to the loss of business to the medical providers, also limits access to patients for important medical services.

There are several notable problems that exist as a result of divergent healthcare markets and information processing relating thereto. The first problem is that medical billing systems use transactions standards developed and maintained by ASC (Accredited Standards Committee) X12, for eligibility determination and the submission of claims, whereas pharmacy systems use transaction standards developed and maintained by the National Council for Prescription Drug Programs (NCPDP) for these two purposes. The bifurcation was validated and strengthened by the HIPAA (Health Insurance Portability and Accountability Act) regulations, which mandate the use of the two separate standards in the two environments. This makes it impossible for a medical billing system to transmit a claim directly to a pharmacy insurance company or their pharmacy benefit manager. A further problem is that medical billing systems are developed assuming batch processing of claim transactions, whereas pharmacy insurance company claims processing systems are developed assuming real-time processing of claim transactions.

Billing systems used by medical service providers such as physicians gather data regarding services to patients over a period of time and then create a batch of claims transactions for these services. These batches are then transmitted as a file to a medical claim clearinghouse entity using a file transfer protocol. The medical claim clearinghouse gathers the data from many of these claim files over a period of time and then creates a batch file including all these claims and transmits the file to a medical insurance company via a file transfer protocol. The medical insurance company processes these claims over a period of time, sometimes extending as long as months. A claim acknowledgement or payment response transactions are created and gathered together based on the submitting medical claim clearinghouse. A file containing the responses to the claims previously transmitted from the specific clearinghouse is transmitted back to the medical claim clearinghouse. The medical claim clearinghouse then splits the response file into various response files to enable transmitting claim responses back to the submitting physician office.

On the other hand, pharmacy claims submitted from pharmacy systems to pharmacy benefit manager systems for adjudication are processed in real time. Pharmacy systems create a single NCPDP claim request transaction and then connect to a pharmacy transaction switch entity and transmit the claim request to the switch. With the connection still open between the pharmacy system and the switch, the claim request transaction is routed and transmitted thereby to a Pharmacy Benefit Manager (PBM) that adjudicates the claim, creates a claim response with acceptance and payment information, and transmits the claim back to the switch. The switch then routes the claim response back to the submitting pharmacy using the still open connection. As a result, pharmacies can determine if a patient is eligible to receive a specific service, exactly how much the patient must pay for the service, and how much the pharmacy will be paid from the PBM within a few seconds.

A further problem is that medical billing systems and medical billing transaction standards are based on identifying products and their related services using a separate Current Procedure Terminology (CPT) code or Health Care Procedure Coding (HCPC) code for a drug product or other type of product being administered or dispensed, and an additional CPT or HCPC code for the related service of administering the drug or dispensing the product. Pharmacy insurance companies or pharmacy benefit managers use one National Drug Code (NDC) registered with the Food and Drug Administration (FDA) to identify both the product and the related service as one unit. An example is that pharmacy insurance companies or their pharmacy benefit managers identify the administration of a vaccine as one NDC code whereas a medical billing system would identify the vaccine product as one CPT code and the related administration service as a separate CPT code. The use of two different code sets for the identification of products and services creates additional barriers for medical providers to offer these pharmacy services and further restricts access for patients to the services.

Yet another problem is that pharmacy insurance company systems and PBMs use the prescription number as the primary identifier for a particular claim transaction, which consists of both the product and related administration fee for one drug. If there are two vaccines administered to a patient, then two prescription numbers are used to identify the claims. Medical Billing Systems do not generate prescription numbers at all, and use one Patient Control Number as the identifier for one claim that may contain multiple vaccine products and multiple administration fees. For example, when a PBM transmits an 835 remittance advice transaction, it uses the prescription number as the primary identifier for each claim consisting of one vaccine and one administration fee. If this 835 remittance advice transaction is received by a medical billing system, it will not know how to match the payments in the ERA to the initial submitted claims.

Accordingly, there is a need in the art for improved systems and methods for billing pharmacy insurance companies or their pharmacy benefit managers for services performed by medical providers and other non-pharmacy providers.

BRIEF SUMMARY

The present disclosure contemplates features by which medical billing systems can submit transactions for services covered under pharmacy benefits with a cross benefit clearinghouse. One aspect of the cross benefit clearinghouse enables medical billing systems to submit claims to insurance companies or their PBM for services that are covered under pharmacy benefits. The cross benefit clearinghouse includes an interface to existing medical claims clearinghouses that enable an existing medical billing system to submit an eligibility request as a standard ASC X12 270 transaction or a medical claim as a standard ASC X12 claim through their existing medical claim clearinghouse, which is then routed to the cross benefit clearinghouse using the same methodology used to route eligibility requests and claims to an existing medical insurance company. The ASC X12 claim may also be directly submitted to the cross benefit clearinghouse.

The cross benefit clearinghouse may implement methods to receive an ASC X12 270 eligibility claim request transaction from a medical claim clearinghouse in real-time and during the same real-time transaction session. It is also possible for the ASC X12 270 eligibility claim request transaction to be received directly from a medical billing system. The methods may include a step of converting the ASC X12 270 eligibility transaction to an NCPDP E1 eligibility request transaction, following by a step of submitting in real-time the NCPDP E1 eligibility transaction to the patient's pharmacy insurance company through the appropriate pharmacy claims switch for that pharmacy insurance company. Furthermore, there may be a step of receiving the NCPDP E1 response from the insurance company and interpreting the eligibility response to determine if the patient has pharmacy insurance coverage. Thereafter, the method may include converting the E1 response to an ASC X12 271 transaction. The ASC X12 transaction may then be returned to the sending medical claim clearinghouse to be routed to the initial submitting medical provider.

The cross benefit clearinghouse may implement methods to receive an ASC X12 270 eligibility claim request transaction, including a CPT code for a particular pharmaceutical product, from a medical claim clearinghouse or directly from a medical billing system in real-time and during the same real-time transaction session. The method may include converting the ASC X12 270 eligibility transaction to an NCPDP B1 claim request transaction. There may also be a step of submitting in real-time the NCPDP B1 claim transaction to the patient's pharmacy insurance company or their pharmacy benefits manager through the appropriate pharmacy claims switch for that pharmacy insurance company. This may be followed by creating and submitting an NCPDP B2 reversal transaction for the NCPDP B1 transaction that was just submitted to the patient's pharmacy insurance company or their pharmacy benefits manager through the appropriate pharmacy claims switch for that pharmacy insurance company. There may be a step of receiving the NCPDP B1 response from the insurance company and interpret the claim response to determine if the patient has pharmacy insurance coverage and if so what the specific coverage is for the submitted product. This may be followed by converting the B1 response to an ASC X12 271 transaction, and then returning the ASC X12 transaction to the sending medical claim clearinghouse to be routed to the initial submitting medical provider.

The cross benefit clearinghouse may implement methods to receive an ASC X12 270 eligibility claim request transaction, including a CPT code for a particular pharmaceutical product, from a medical claim clearinghouse or directly from a medical billing system in real-time and during the same real-time transaction session. The method may include converting the ASC X12 270 eligibility transaction to an NCPDP D1 predetermination of benefits request transaction. There may also be a step of submitting in real-time the NCPDP D1 benefits predetermination transaction to the patient's pharmacy insurance company or their pharmacy benefits manager through the appropriate pharmacy claims switch for that pharmacy insurance company. There may be a step of receiving the NCPDP D1 response from the insurance company and interpret the claim response to determine if the patient has pharmacy insurance coverage and if so what the specific coverage is for the submitted product. This may be followed by converting the D1 response to an ASC X12 271 transaction, and then returning the ASC X12 transaction to the sending medical claim clearinghouse to be routed to the initial submitting medical provider. The cross benefit clearinghouse may also implement methods to process any new NCPDP transaction set that is promulgated that serves the purpose of checking the eligibility and benefits coverage for a particular patient and or a particular drug product.

The cross benefit clearinghouse may also implement methods to receive batches of ASC X12 837 claims transactions from a medical claims clearinghouse. The method may include validating that the batch file meets all X12 837 standard requirements. Then, there may be a step of splitting the X12 837 claim transaction into a separate transaction for each 837 service line, and storing the data necessary to retain the relationship between the individual service lines to the initial 837 claim. The method may further include converting each 837 service line into either an NCPDP B1 request or NCPDP S1 request according to pharmacy insurance plan or PBM specific coding rules, and creating and assigning a prescription number or service number to each service line. The method may also include submitting each B1 request or S1 request in real time to the appropriate pharmacy insurance plan or PBM. Then, the method may include receiving the B1 response or S1 response from the pharmacy insurance plan or PBM, and processing the B1 response or S1 response for conversion to the appropriate X12 277CA or X12 835 transaction. The method may also include batching the X12 277CA or X12 835 transactions for each submitter into a file and transmit the file to the initial submitter.

The cross benefit clearinghouse may also implement methods to receive, in a real time transaction, an ASC X12 837 claim from a medical claims clearinghouse or directly from a medical billing system. The method may include a step of validating that the X12 837 transaction meets the X12 standard requirements. There may be a step of splitting the X12 837 claim transaction into a separate transaction for each 837 service line and storing the data necessary to retain the relationship between the individual service lines to the initial 837 claim. The method may then proceed to converting each 837 service line into either an NCPDP B1 Request or NCPDP S1 Request according to pharmacy insurance plan or PBM specific coding rules and create and assign a prescription number or service number to each service line. Furthermore the method may include submitting each B1 request or S1 request in real time to the appropriate pharmacy insurance plan or PBM, and receive the B1 response or S1 response from the pharmacy insurance plan or PBM. Process the B1 response or S1 response and convert to the appropriate X12 277CA transaction or X12 835 transaction. The method may also include batching the X12 277CA or X12 835 transactions for each submitter into a file and transmit the file to the initial submitter.

The cross benefit clearinghouse may also implement additional steps for records retention. In particular, there may be a step of storing the claims identifiers, data content and their relationship to the batch file the claims were submitted in. Additionally, there may be steps of storing the relationship of the service lines to the claims that they were split from. Another possible step is storing the prescription/service numbers that the system generates and their relationship to the service lines that are split from the claim files. Furthermore, there may be steps of mapping and combining the 835 remittance data later returned from the pharmacy which is based on individual service lines using the prescription/service number into 835 remittance data that is organized around the initial medical claim that was submitted and with the original claim identifiers submitted with the claim.

The cross benefit clearinghouse may further implement various record processing steps. These include establishing an interface to existing PBM systems that enable downloading of files containing ASC X12 835 transactions. Furthermore, there may be steps of processing the 835 transactions including the use of stored identifier information to enable mapping of prescription/service numbers in the 835 to the claim identifiers originally submitted with the claims. Combining separate 835 payment service lines into one X12 835 that references the initial X12 837 claim submitted may also be implemented.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of the presently preferred embodiments of the disclosure, and is not intended to represent the only form in which they may be developed or utilized. The description sets forth the functions in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
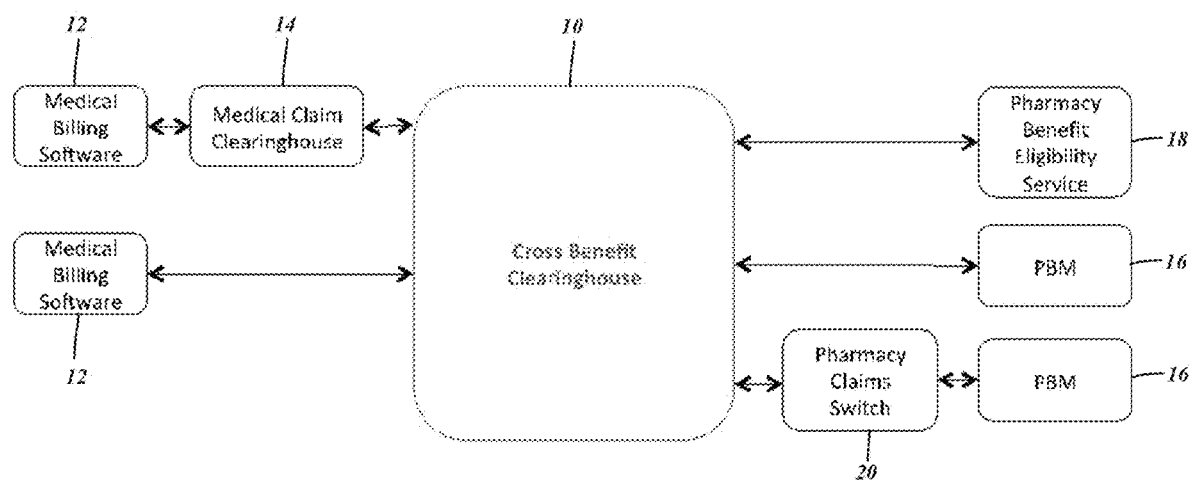
FIG. 1 is a block diagram illustrating an exemplary Cross Benefit Clearinghouse and the components to which it is connected for medical billing systems to process pharmacy benefits.

With reference to the block diagram of FIG. 1, a cross benefit clearinghouse 10 is a software system that can be implemented using any programming language and deployed on any hardware and operating system platform. Any healthcare entity providing services covered under the pharmacy benefit and using a medical billing software application 12 that submits X12 transactions can take advantage of the various methods of the present disclosure, including, but not limited to physician offices, pharmacy retail clinics, specialty pharmacies, and public health department clinics. Transactions can be submitted to the cross benefit clearinghouse 10 in real-time or batch files directly from medical billing software systems 12 or through a medical claim clearinghouse 14.

The cross benefit clearinghouse 10 can exchange messages with any entity processing pharmacy benefit claims and/or pharmacy benefit eligibility transactions. These include but are not limited to various pharmacy benefit managers (PBMs) 16, pharmacy benefit eligibility service providers 18, and pharmacy benefit insurance companies.

The cross benefit clearinghouse 10 can submit and receive transactions in real time or batch files directly with PBMs 16 and pharmacy benefit eligibility service providers 18 or through pharmacy transaction switches 20. The cross benefit clearinghouse 10 can be implemented as a stand-alone system, an integral part of a medical billing system, an integral part of a medical claims clearinghouse, an integral part of a pharmacy claims switch, an integral part of a pharmacy benefit manager or as an integral part of a pharmacy benefit insurance adjudication system.

Figure 2:
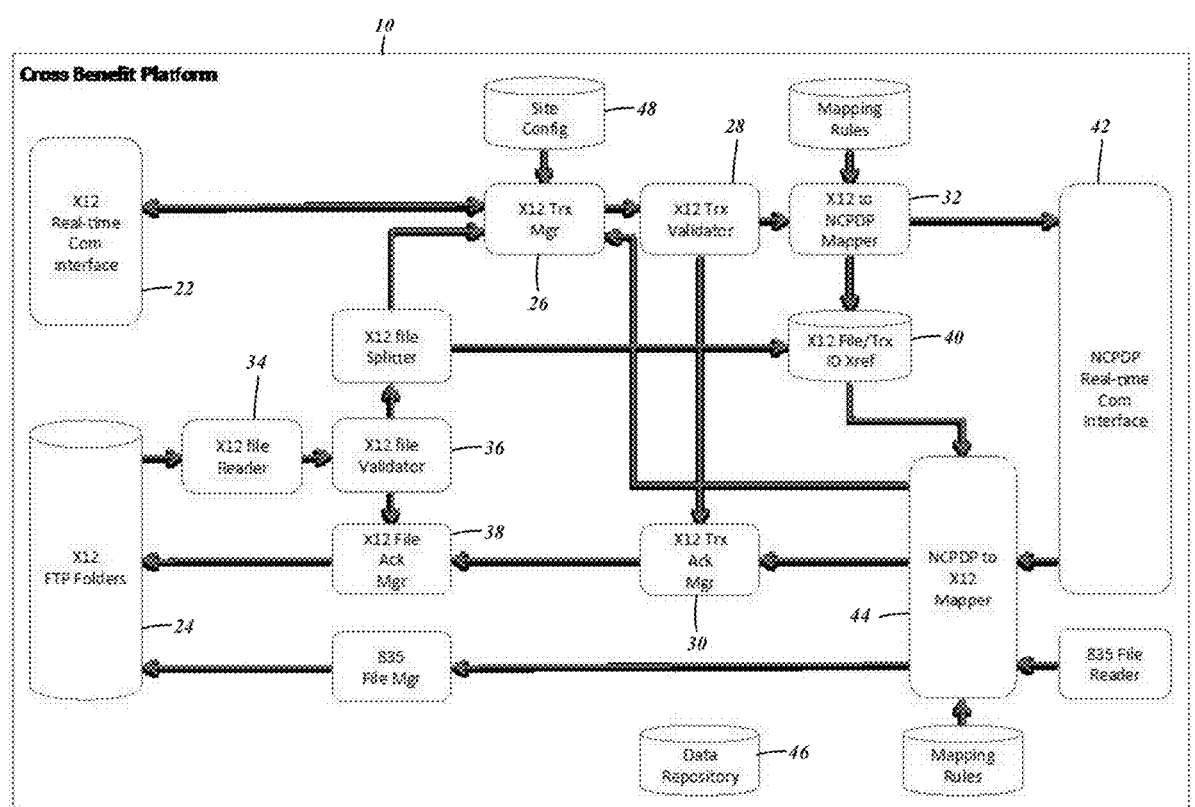
FIG. 2 is a block diagram illustrating the components of the Cross Benefit Clearinghouse in accordance with one embodiment of the present disclosure.

Referring to the block diagram of FIG. 2, the cross benefit clearinghouse system 10 is comprised of various logical components, as detailed more fully below. Generally, there is an X12 real-time communication interface 22, X12 FTP folders 24, an X12 transaction manager 26, an X12 transaction validator 28, an X12 transaction acknowledgement manager 30, an X12 to NCPDP mapper 32, an X12 file reader 34, an X12 file validator 36, an X12 file acknowledgement manager 38, an X12 file/transaction reference data store 40, an NCPDP real-time communications interface 44, an NCPDP to X12 mapper 44, and a data repository 46.

The X12 real-time communication interface 22 provides a real-time communications interface to the cross benefit clearinghouse 10 from a medical billing software system 12 or the medical claims clearinghouse 14. The interface can be implemented as a Web Service, HTTP (HyperText Transfer Protocol) Post of XML (eXtensible Markup Language), HTTP Post of X12 Message, or TCP/IP (Transmission Control Protocol/Internet Protocol) socket connection.

The cross benefit clearinghouse 10 includes X12 FTP folders 24. One of the interface points with outside systems is an FTP subsystem with folders for each submitter and for the various types of files and reports for each submitter. The FTP folders 24 can be implemented to use any encryption methodology for the files themselves or for the communication session.

The X12 transaction manager 26 uses sender and receiver information from the message as well as a site configuration data store 48 to control the processing of the message by the cross benefit clearinghouse 10. X12 transactions can be validated against appropriate X12 standard edits with the X12 transaction validator 28. If the transaction does not pass the edits for the specific transaction, the message is passed to the X12 transaction acknowledgement manager 30. The processing of all transactions through the clearinghouse creates appropriate X12 acknowledgment transactions which are tracked by the transaction acknowledgment manager 30 and merged into appropriate files.

The X12 to NCPDP mapper 32 is a transaction format and content mapping engine that uses a series of database tables and data transformation routines to perform a number of important functions including splitting X12 837 claims into individual service lines, mapping the X12 837 service lines into NCPDP S1 claim requests, NCPDP B1 claim requests, NCPDP D1 benefit predetermination requests or any future NCPDP transactions set devised to perform the same functionality as the D1, mapping the X12 270 eligibility transactions into NCPDP E1 eligibility requests, or NCPDP B1 claim requests or NCPDP D1 benefit predetermination requests, mapping content of X12 837 claims into appropriate NCPDP B1 claim or NCPDP S1 claim content. The creation of necessary transaction trace numbers and identifiers and mapping of X12 code sets into appropriate NCPDP code sets, mapping of CPT or HCPCS codes into appropriate NDC codes, mapping of X12 billing quantities into appropriate NCPDP billing quantities, mapping of X12 units of measure into appropriate NCPDP units of measure and storing the initial and resulting data and relationship information regarding all the mapped transactions and their identifiers. Although references will be made to the NCPDP standardized claim requests, benefit predeterminations requests, eligibility requests, and so on, these are understood to be by way of example only and not of limitation. To the extent that any future standards are developed and utilized, those having ordinary skill in the art will recognize the needed adaptations of the various features of the present disclosure to such newer standards.

The X12 file reader 34 interfaces with the FTP folder subsystem 24 to select and process X12 837 files. The X12 file reader 34 also manages the processing of all transactions in the file and stores relationship information of the claims included in the file. All X12 files received in the clearinghouse can be validated against X12 standards, including submitter and payer specific rules, by the X12 file validator 36. Results of the validation are passed to the X12 file acknowledgement manager 38. All X12 files processed by the clearinghouse are acknowledged back to the submitter with the appropriate TA1 or 999 transaction using the X12 file acknowledgement manager 38. As X12 files are processed and split into individual claims and claims are split into individual service lines and then the service lines are mapped to NCPDP B1 or S1 transactions the relationship between all files, records and identifiers between associated records are stored in the X12 file/transaction reference data store 40.

The NCPDP real-time communication interface 42 provides a real-time interface from the cross benefit clearinghouse 10 to PBMs 16, pharmacy switches 20 and pharmacy benefit insurance plans. The real-time interface can be implemented using any protocol and encryption methodology.

The NCPDP to X12 mapper 44 is a transaction format and content mapping engine that uses the data stored from the processing of transactions by the X12 to NCPDP mapper 44, a series of database tables and data transformation routines to perform a number of important functions including mapping of NCPDP E1 or D1 response transactions into X12 271 response transactions, mapping of B1, S1 response transactions into X12 277CA or X12 835 transactions, combining multiple NCPDP B1 or S1 response transactions into single X12 277CA or X12 835 transactions when multiple services were sent in one original X12 837 claim transaction, mapping of NCPDP quantities into X12 billed quantities, mapping of NCPDP units of measure into X12 units of measure, mapping of NDC codes to CPT or HCPC codes. The NCPDP to X12 mapper may be implemented to work with any future NCPDP transactions sets designed to provide eligibility or predetermination of benefits.

All files and all versions of transactions as they are processed through the mapping process are stored in the data repository 46 to be used in reporting and other administrative functions.

The cross benefit clearinghouse 10 enables four distinct services that can be implemented as standalone services and are not dependent on each other in any way. These include cross benefit eligibility, cross benefit coverage predetermination, cross benefit claim submission, and cross benefit electronic remittance advice processing. Each of these services will be described in further detail below.

Figure 3:
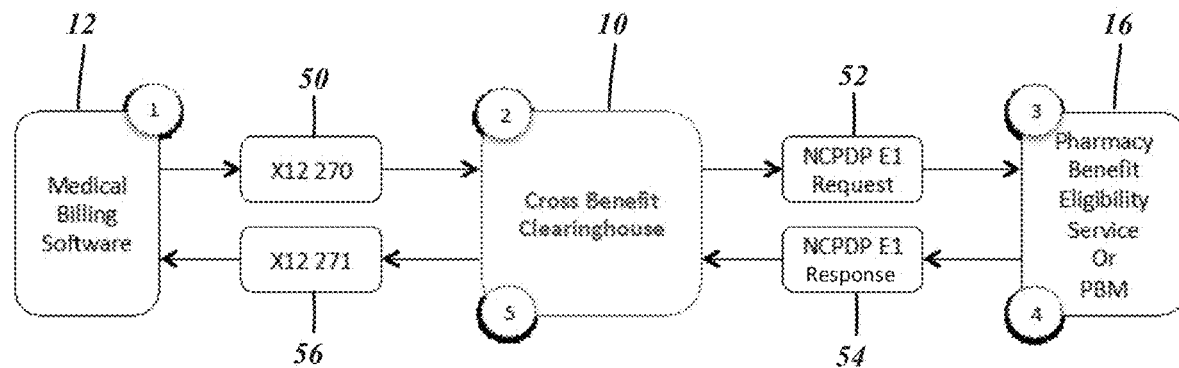
FIG. 3 is a process sequence diagram showing an implementation of a cross benefit eligibility service.

It is contemplated that the cross benefit eligibility service enables providers to use their medical billing software system 12 to determine a patient's pharmacy benefit eligibility status. The steps of this service are shown in the diagram of FIG. 3. First, the providers submit a real time eligibility transaction as an X12 270 transaction 50 to the cross benefit clearinghouse 10. Then, the X12 270 transaction 50 is mapped to NCPDP E1 request transactions 52 and transmitted to the PBM 16 or pharmacy benefit eligibility service 18 while leaving the initial real-time session open from the provider system. Thereafter, the PBM 16 or pharmacy benefit eligibility service receives the NCPDP E1 request 52 and processes it, creating an appropriate NCPDP E1 response 54. The PBM 16 or pharmacy benefit eligibility service 18 then transmits the NCPDP E1 response 54 back to the cross benefit clearinghouse 10 in the same real-time session. The cross benefit clearinghouse 10 maps the NCPDP E1 response 54 transaction to an X12 271 transaction 56 and returns the transaction to the sending provider system in the initial real-time session.

Other implementations of this service include the medical billing software 12 sending the X12 270 transaction to a medical claims clearinghouse, which then sends the X12 270 transaction to the cross benefit clearinghouse 10. The cross benefit clearinghouse 10 returns the X12 271 transaction to the medical claims clearinghouse 14, which forwards the same to the sending provider. Additionally, the cross benefit clearinghouse 10 can send the NCPDP E1 request to the pharmacy claims switch 20 that routes the transaction to the PBM 16. The PBM 16 returns the NCPDP E1 response transaction to the pharmacy claims switch 20, which routes the transaction back to the cross benefit clearinghouse 10. The cross benefit clearinghouse 10 maps the NCPDP E1 response transaction to an X12 271 transaction and returns the transaction to the sending provider system in the initial real-time session.

Figure 4:
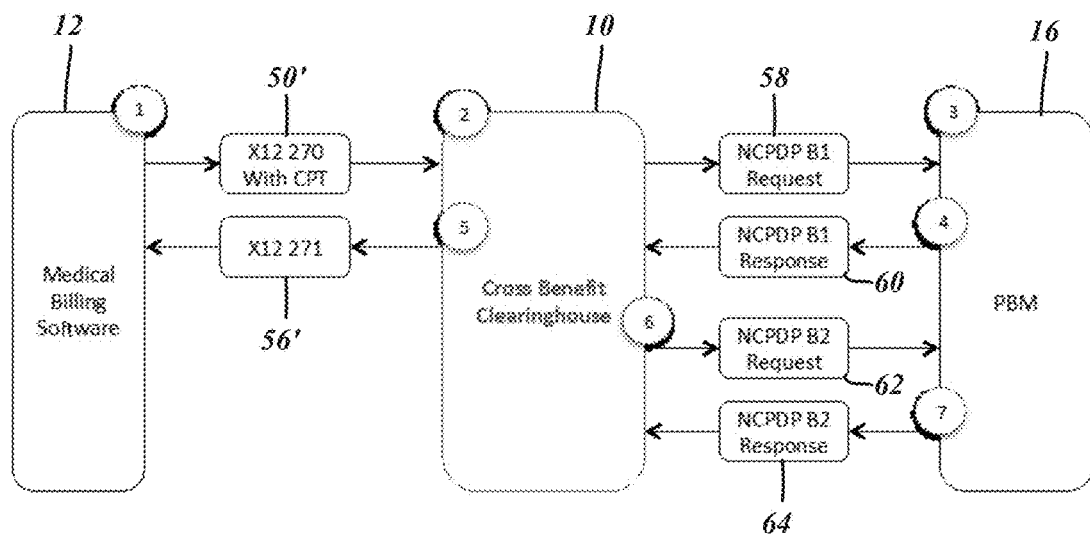
FIG. 4 is a process sequence diagram showing an implementation of a cross benefit coverage pre-determination service.

The diagram of FIG. 4 describes the service of cross benefit coverage pre-determination. This is contemplated to enable providers to determine a patient's financial responsibility for a particular drug product or service by submitting a real time X12 270 eligibility transaction that includes a CPT code for the pharmaceutical product that the provider wishes to determine coverage. The cross benefit clearinghouse 10 returns the specific coverage information for the patient and the submitted product. First, the medical billing software 12 submits a real time eligibility transaction including a CPT code as an X12 270 transaction 50' to the cross benefit clearinghouse 10. Then, the X12 270 transaction is mapped to an NCPDP B1 request transaction 58 and transmitted to a PBM 16 while leaving the initial real-time session open from the medical billing system 12. The PBM 16 receives the NCPDP B1 request 58 and processes it, creating the appropriate NCPDP B1 response 60. Additionally, the PBM 16 transmits the NCPDP B1 response 60 back to the cross benefit clearinghouse 10 in the same real-time session. The cross benefit clearinghouse maps the NCPDP B1 response transaction to an X12 271 transaction 56' and returns the transaction to the sending provider system in the initial real-time session. The cross benefit clearinghouse 10 then creates an NCPDP B2 reversal transaction 62 from the previously processed NCPDP B1 claim transaction 58 and transmits the transaction to the PBM 16 that processed the claim transaction. The PBM 16 receives the reversal transaction 62, processes the reversal and sends the NCPDP B2 reversal response transaction 64 back to the cross benefit clearinghouse 10.

An alternative implementation of the service also involves various alternate procedures. In further detail, the cross benefit clearinghouse 10 submits an NCPDP D1 predetermination of benefits transaction instead of a NCPDP B1 claim transaction. In this implementation, the NCPDP B2 reversal transaction is not sent. The medical billing software 12 may also send the X12 270 transaction to the medical claims clearinghouse 14, which then sends the X12 270 transaction to the cross benefit clearinghouse 10. The cross benefit clearinghouse 10 returns the X12 271 transaction to the medical claims clearinghouse 14, which forwards it to the sending provider. Furthermore, the cross benefit clearinghouse 10 sends the NCPDP B1 request to the pharmacy claims switch 20 that routes the transaction to the PBM 16. The PBM 16 returns the NCPDP B1 response transaction to the pharmacy claims switch 20 which routes the transaction back to the cross benefit clearinghouse 10. Additional alternative implementations of the service would substitute for the NCPDP D1 transaction any new NCPDP transaction set that is designed to perform a patient benefit determination for a specific drug product.

The contemplated cross benefit claim submission service enables medical providers to submit claim transactions in real-time or batch files as X12 837 transactions for services covered under a patient's pharmacy benefit. The cross benefit clearinghouse 10 returns the appropriate file and/or claim acknowledgements and remittance information.

Figure 5:
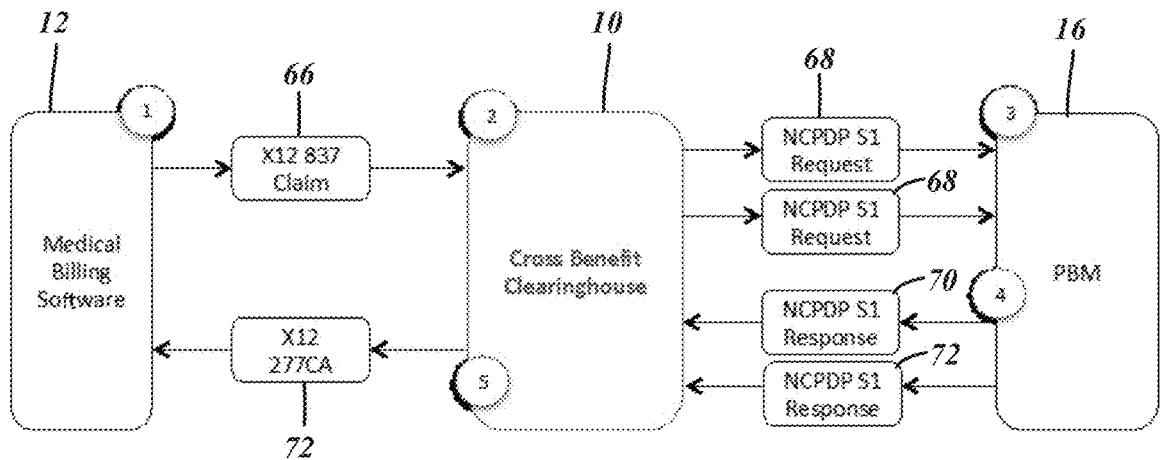
FIG. 5 is a process sequence diagram showing an implementation of a real-time cross benefit claim submission service.

The diagram of FIG. 5 shows the real-time cross benefit claim submission service. First, the medical billing software 12 submits a real time X12 837 claim transaction 66 to the cross benefit clearinghouse 10. The X12 837 transaction 66 is mapped into one or more NCPDP S1 or B1 claim request transactions 68. One NCPDP S1 or B1 claim request 68 is created for each X12 837 service line in the submitted claim. The multiple NCPDP S1 request transactions 68 are transmitted to a PBM 16 sequentially in real time sessions while leaving the initial real-time session open from the medical billing system 12. The PBM 16 then receives each of the NCPDP S1 request transactions 68, processes the request and creates the appropriate NCPDP S1 response message 70. The PBM 16 transmits the NCPDP S1 response transactions 70 back to the cross benefit clearinghouse 10 in the same real-time session it received each transaction. The cross benefit clearinghouse 10 maps the one or more NCPDP S1 response transactions 70 to one X12 277CA transaction 72 and returns the transaction to the sending provider system in the initial real-time session. NCPDP S1 response transactions 70 with a Rejected status create an Accepted 277CA and the transaction is held in a data store to be used to add Denial data to a subsequent X12 835 transactions for the submitted X12 837 claim.

This service also includes additional procedures. In particular, the medical billing system 12 transmits the claim to a medical claims clearinghouse 14 which transmits the claim to the cross benefit clearinghouse 10. The X12 837 claim service lines are mapped into NCPDP S1 or B1 request transactions and the PBM 16 responds back with NCPDP S1 or B1 response transactions. The NCPDP S1 or B1 request transactions are transmitted to the pharmacy claims switch 20 that forwards the requests to the appropriate PBM 16 and accepts and routes the S1 or B1 responses from the PBM 16 to the cross benefit clearinghouse 12. Instead of an X12 277CA transaction being returned to the medical billing software 12, an X12 835 transaction is created and returned to the medical billing software 12. If one or more of the S1 or B1 response transactions have a Rejected status, the associated 835 service payment line has a $0 payment with an adjustment code mapped to the reject reason code.

Figure 6:
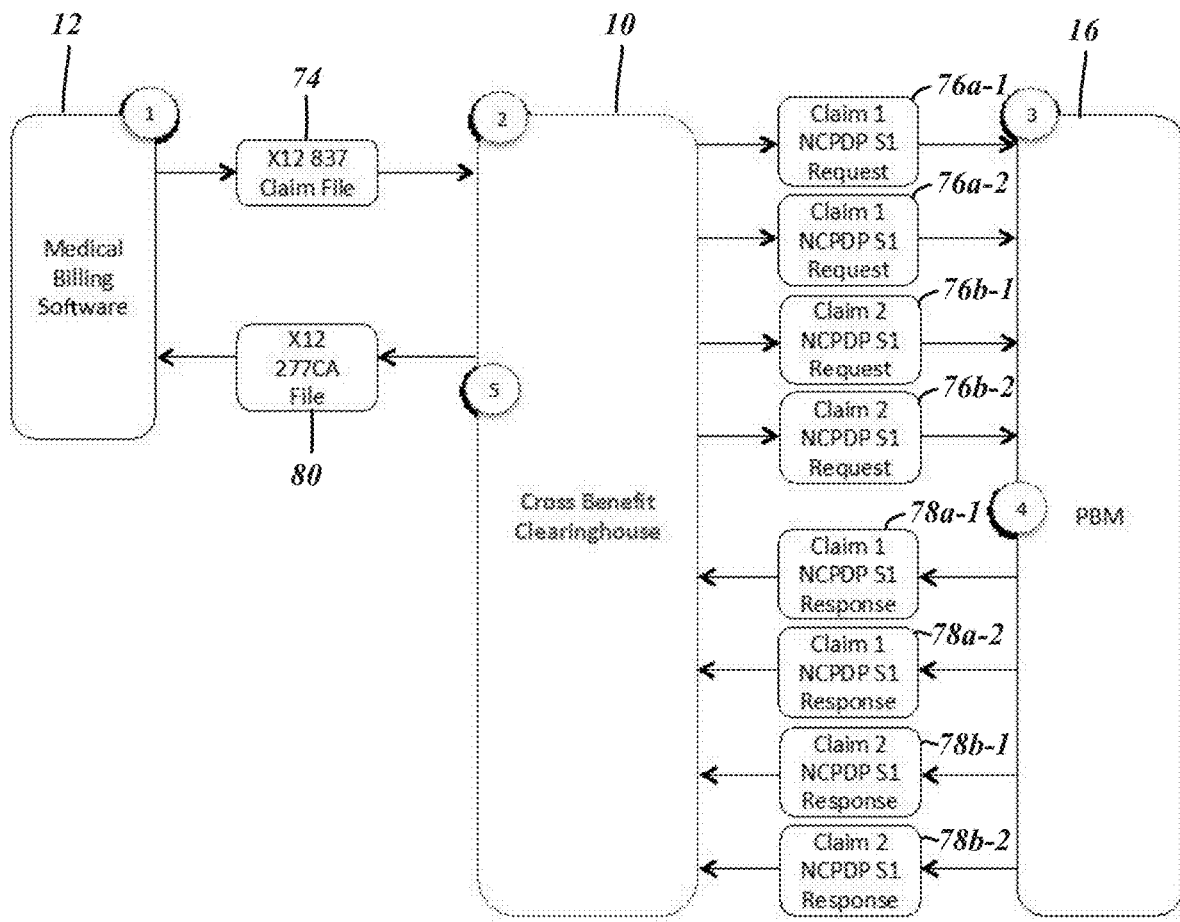
FIG. 6 is a process sequence diagram showing an implementation of a batch cross benefit claim submission service.

The diagram of FIG. 6 shows the batch cross benefit claim submission service. The medical billing software 12 submits an X12 837 claim batch file 74 containing one or more X12 837 claims to the cross benefit clearinghouse 10. The X12 837 file 74 is split into individual X12 837 claims, which are each mapped into one or more NCPDP S1 or NCPDP B1 claim request transactions 76. One NCPDP S1 or B1 claim request 76 is created for each X12 837 service line in the submitted claim. The multiple NCPDP S1 or B1 request transactions are transmitted to the PBM 16 sequentially in real time sessions while leaving the initial real-time session open from the medical billing system 12. The PBM 16 receives each NCPDP S1 or B1 request transaction, processes the request and creates an appropriate NCPDP S1 or B1 response message 78. The PBM transmits the NCPDP S1 or B1 response transaction 78 back to the cross benefit clearinghouse 10 in the same real-time session it received each transaction. The cross benefit clearinghouse 10 maps the one or more NCPDP S1 or B1 response transactions to one X12 277CA or X12 835 transaction 80 for each submitted X12 837 claim, batches the X12 277CA or 835 transactions together that relate to the X12 837 claims that were submitted in the 837 file and writes the 277CA or 835 file to an FTP folder for the medical claims system that submitted the 837 file to retrieve. NCPDP S1 or B1 response transactions 78 with a Rejected status create an Accepted 277CA and the transaction is held in a data store to be used to add Denial data to a subsequent X12 835 transactions for the submitted X12 837 claim.

Additional procedures are also implemented in the batch benefit claim submission service. The medical billing system 12 transmits the claims to a medical claims clearinghouse 14 which sends the X12 837 claim file to the cross benefit clearinghouse 10. The X12 837 claim service lines are mapped into NCPDP S1 or B1 request transactions and the PBM 16 responds back with NCPDP S1 or B1 response transactions. The NCPDP 1 or B1 request transactions are transmitted to a pharmacy claims switch 20 that forwards the requests to the appropriate PBM 16 and accepts and routes the S1 or B1 responses from the PBM 16 to the cross benefit clearinghouse 10. Instead of an X12 277CA file being returned to the medical billing software 12, an X12 835 file is created and returned to the medical billing software 12. If one or more of the S1 or B1 response transactions have a Rejected status, the associated 835 service payment line has a $0 payment with an adjustment code mapped to the reject reason code. The cross benefit clearinghouse 10 can also combine multiple X12 837 service lines, one for a drug product and the other for the administration of the drug, into one NCPDP B1 request with the appropriate submitted ingredient cost and submitted administration fee.

Figure 7:
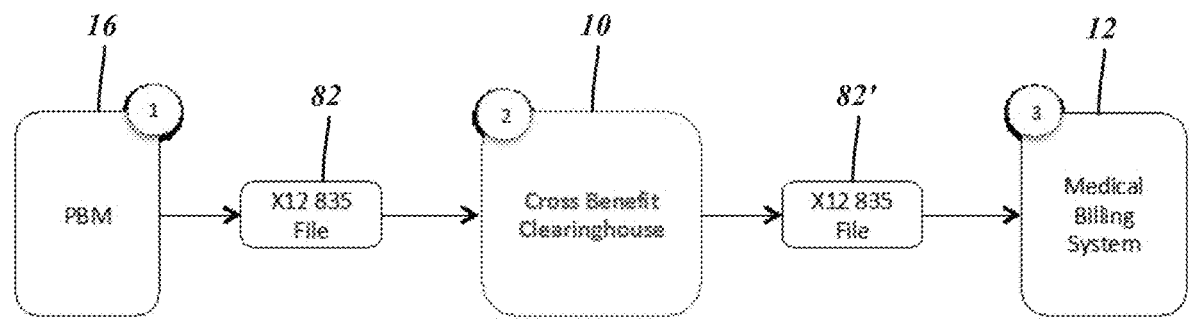
FIG. 7 is a process sequence diagram showing an implementation of an electronic remittance advice service.

FIG. 7 illustrates the process for electronic remittance advice, which enables medical billing systems 12 to receive X12 835 ERA (electronic remittance advice) files 82 that are formatted and contain data that references the X12 837 claim identifiers that were included in the 837 claims submitted to PBMs 16 through the cross benefit clearinghouse 10. The PBM 16 creates and transmits an X12 835 ERA file 82 containing one 835 claim payment segment and one service payment segment for each NCPDP B1 or S1 that it processed to the cross benefit clearinghouse 10. The cross benefit clearinghouse 10 uses stored data from the received X12 837 files and submitted NCPDP S1 or B1 claim request and response transactions along with the 835 data of the PBMs 16 to map the 835 transactions into new X12 835 transactions. The new 835 data is saved to the appropriate FTP folder for the medical billing system 12 to retrieve. When processing 835 claim payments for multiple B1 or S1 claims that were included in one submitted 837 claim, the 835 claim payments and associated data are combined into one 835 claim payment with one 835 service payment record for each B1 or S1 claim that was included in the original 837 claim. The initial patient control number/claim identifier that was submitted in the initial X12 837 claim is added to the new 835 claim payment, and the medical billing system 12 retrieves the X12 835 from the cross benefit clearinghouse 10 FTP folders.

Alternatively, the newly created X12 835 file is transmitted to a medical claims clearinghouse 14, where it is stored for the medical billing system 12 to retrieve.

Furthermore, claims may be submitted from a pharmacy billing system 16 in NCPDP format to the cross benefit clearinghouse 10. The claims are mapped to X12 837 claims and submitted to the medical insurance benefit payer. During the mapping process, the NCPDP B1 prescription number identifiers are stored and mapped to X12 837 patient control number identifiers and when appropriate, one NCPDP claim will be mapped to multiple X12 837 service lines. When X12 835 remittance files are received from the medical insurance benefit payer at the cross benefit clearinghouse 10, the stored NCPDP prescription numbers are looked up and are used to replace the X12 patient control numbers that were sent in the 835 remittance file.

The particulars shown herein are by way of example and for purposes of illustrative discussion of the embodiments of the present disclosure only and are presented in the cause of providing what is believed to be the most useful and readily understood description of the principles and conceptual aspects thereof. In this regard, no attempt is made to show details of the various embodiments with more particularity than is necessary for the fundamental understanding of the present disclosure, the description taken with the drawings making apparent to those skilled in the art how the several forms may be embodied in practice.

What is claimed is:

1. A method for a cross benefit clearinghouse computer system to process batches of medical insurance claims from a medical claims clearinghouse system received over one or more sessions and during the batch processing, the method comprising:

validating that the batch file complies with requirements of a first predetermined standard on the cross benefit clearinghouse computer system;

splitting the batch file into individual medical insurance claims, each of the medical insurance claims including one or more service lines;

splitting the medical insurance claims into separate transactions for each of the one or more service lines thereof on the cross benefit clearinghouse computer system;

storing in a transaction reference data store on the cross benefit clearinghouse computer system, associations between the individual service lines and corresponding ones of the medical insurance claims from which the one or more service lines were split;

converting each of the service lines into a pharmacy insurance claim request in accordance with coding rules for at least one of a pharmacy insurance plan and a pharmacy benefit manager;

assigning either one of a prescription number or a service number to each service line on the cross benefit clearinghouse computer system;

submitting the pharmacy insurance claim requests in real time sessions with a computer system of the respective one of the pharmacy insurance plan and the pharmacy benefit manager separate from the plurality of sessions in which the medical insurance claims were received from the medical claims clearinghouse system;

receiving pharmacy insurance claim responses from the respective one of the computer systems of the pharmacy insurance plan and the pharmacy benefit manager for each of the submitted pharmacy insurance claim requests;

converting, on the cross benefit clearinghouse computer system, the pharmacy insurance claim responses to medical insurance claim acknowledgement transactions based upon the associations in the transaction reference data store;

batching, on the cross benefit clearinghouse computer system, the medical insurance claim acknowledgment transactions for each submission of the pharmacy insurance requests into a file; and transmitting the file to a computer system of an originator of the medical insurance claims transactions.

2. The method of claim 1, wherein:
the medical insurance claims transactions are ASC X12 837 claims transactions; and
the first predetermined standard is ASC X12 837.

3. The method of claim 1, wherein the pharmacy insurance claim request is one of an NCPDP B1 request and a NCPDP S1 request.

4. The method of claim 1, wherein the pharmacy insurance claim response is one of a NCPDP B1 response and a NCPDP S1 response.

5. The method of claim 1, wherein the medical insurance acknowledgment transaction is one of a ASC X12 277CA transaction and a ASC X12 835 transaction.

6. A method to process in a real time transaction on a cross benefit clearinghouse computer system a medical insurance claim from a medical claims source and during the real-time processing:
validating, on the cross benefit clearinghouse computer system, that the medical insurance claim complies with requirements of a first predetermined standard;
splitting the medical insurance claim into a separate transaction for each service line thereof on the cross benefit clearinghouse computer system;
storing, in a transaction reference data store, associations between individual service lines and the medical insurance claim from which the service lines were split;
converting on the cross benefit clearinghouse computer system each of the service lines into a pharmacy insurance claim request according to predetermined coding rules;
assigning either one of a prescription number or a service number to each service line on the cross benefit clearinghouse computer system;
submitting each of the pharmacy insurance claim requests in real time sessions with a computer system of a pharmacy insurance processor over respective sessions separate from the plurality of sessions in which the medical insurance claims were received from the medical claim source;
receiving on the cross benefit clearinghouse computer system a pharmacy insurance claim response from the computer system of the pharmacy insurance processor corresponding to the submitted pharmacy insurance claim requests;
converting the pharmacy insurance claim response to medical insurance acknowledgment transactions based upon the associations in the transaction reference data store; and
batching the medical insurance acknowledgement transactions for each submitter into a file on the cross benefit clearinghouse computer system as received over the respective sessions taking place in real time with the computer system of the pharmacy insurance processor;
transmitting the file to a computer system of an originator of the medical insurance claim transactions in a subsequent session separate from the respective sessions with the computer system of the pharmacy insurance processor.

7. The method of claim 6, wherein:
the medical insurance claim is an ASC X12 837 claim; and
the first predetermined standard is ASC X12.

8. The method of claim 6, wherein the medical claims source is a medical claims clearinghouse.

9. The method of claim 6, wherein the medical claims source is a medical billing system.

10. The method of claim 6, wherein the pharmacy insurance claim request is an NCPDP B1 request.

11. The method of claim 6, wherein the pharmacy insurance claim request is an NCPDP S1 request.

12. The method of claim 6, wherein the predetermined coding rules are specific to the pharmacy insurance processor.

13. The method of claim 12, wherein the pharmacy insurance processor is one of a pharmacy insurance plan and a pharmacy benefits manager.

14. The method of claim 6, wherein the medical insurance acknowledgment transaction is one of an ASC X12 277CA transaction and a ASC X12 835 transaction.

* * * * *